US007789821B2

(12) United States Patent
Browning

(10) Patent No.: US 7,789,821 B2
(45) Date of Patent: *Sep. 7, 2010

(54) APPARATUS AND METHOD FOR TREATING FEMALE URINARY INCONTINENCE

(75) Inventor: James Browning, Glasgow (GB)

(73) Assignee: Gyne Ideas Ltd., Wingrave, Buchinghamshire (GB)

( * ) Notice: Subject to any disclaimer, the term of this patent is extended or adjusted under 35 U.S.C. 154(b) by 1342 days.

This patent is subject to a terminal disclaimer.

(21) Appl. No.: 11/199,061

(22) Filed: Aug. 8, 2005

(65) Prior Publication Data

US 2006/0041185 A1    Feb. 23, 2006

Related U.S. Application Data

(63) Continuation of application No. 10/398,992, filed as application No. PCT/GB01/04554 on Oct. 12, 2001, now Pat. No. 6,960,160.

(30) Foreign Application Priority Data

Oct. 12, 2000    (GB)    .................... 0025068.8

(51) Int. Cl.
*A61B 19/00*    (2006.01)
*A61F 2/00*    (2006.01)

(52) U.S. Cl. ........................... 600/37; 600/30

(58) Field of Classification Search ............ 600/29–31, 600/37; 128/DIG. 25, 897–898; 606/139–144, 606/151–158, 232–233
See application file for complete search history.

(56) References Cited

U.S. PATENT DOCUMENTS

| 3,054,406 A | 9/1962 | Usher |
| 3,888,975 A | 6/1975 | Ramwell |
| 3,911,911 A | 10/1975 | Scommegna |
| 3,913,573 A | 10/1975 | Gutnick |
| 3,916,899 A | 11/1975 | Theeuwes et al. |
| 3,993,058 A | 11/1976 | Hoff |
| 4,233,968 A | 11/1980 | Shaw |
| 4,633,873 A | 1/1987 | Dumican et al. |
| 4,646,731 A | 3/1987 | Brower |
| 4,655,221 A | 4/1987 | Devereux |

(Continued)

FOREIGN PATENT DOCUMENTS

DE    10019604 A1    10/2001

(Continued)

OTHER PUBLICATIONS

U.S. Appl. No. 60/279,794, filed Mar. 2001, Klutke et al.

(Continued)

*Primary Examiner*—John P Lacyk
(74) *Attorney, Agent, or Firm*—Burns & Levinson LLP; Ronda P. Moore

(57) ABSTRACT

The present invention provides a surgical implant and method for supporting the urethra, the implant comprising a suburethral support suspended between two soft tissue anchors that do not penetrate the lower abdominal wall and are attached at either side of the sururethral support. The soft tissue anchors retain each anchor in soft tissue, suspending each side of the suburethrasl support. The suburethral support passes under the urethra to support the urethra. The implant has uses including treating urinary incontinence and uterovasginal prolapse.

11 Claims, 16 Drawing Sheets

U.S. PATENT DOCUMENTS

Figure 1:
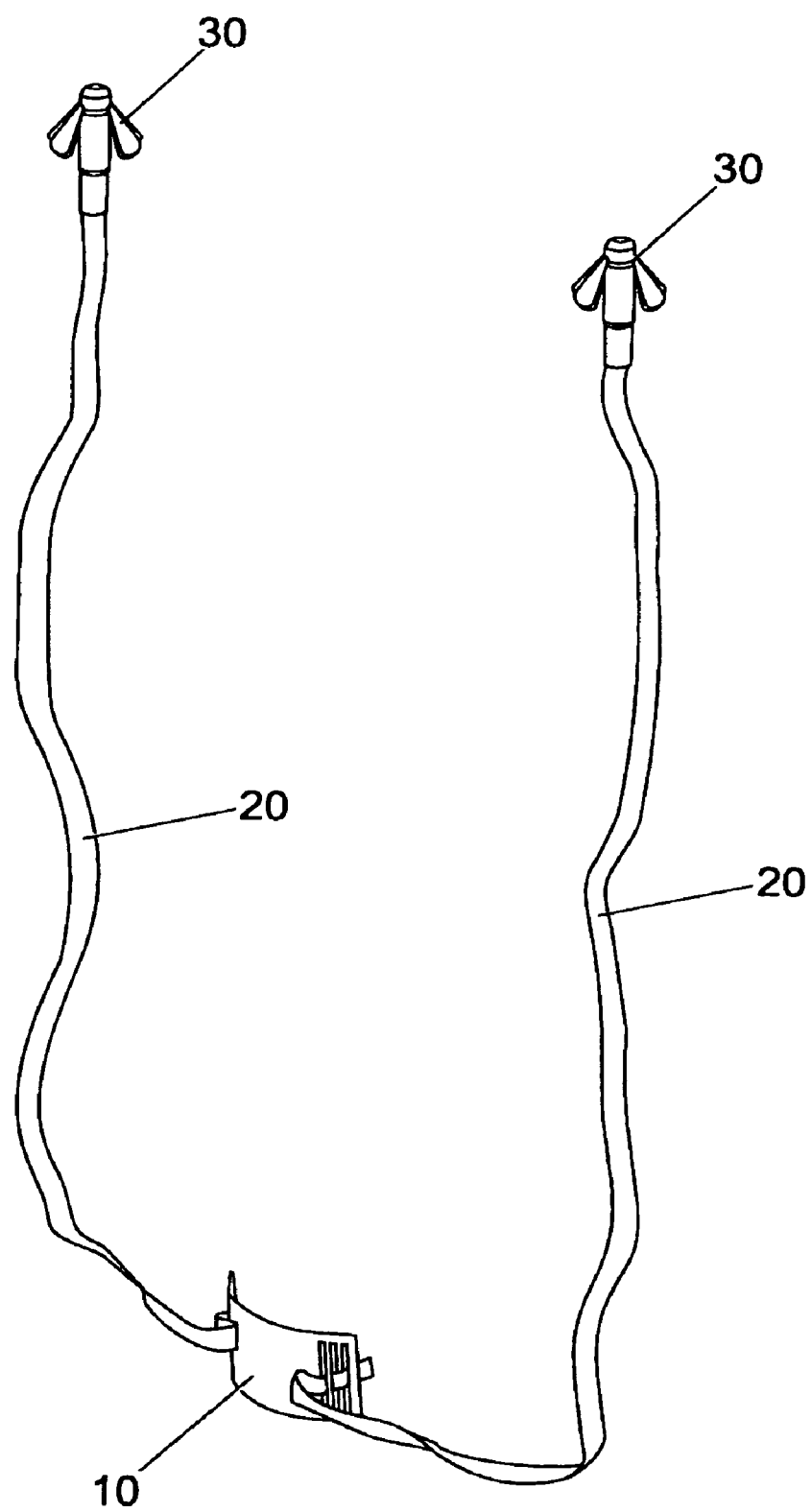

| | | | |
|---|---|---|---|
| 4,857,041 A | 8/1989 | Annis et al. | |
| 4,938,760 A | 7/1990 | Burton et al. | |
| 5,013,292 A | 5/1991 | Lemay | |
| 5,112,344 A | 5/1992 | Petros | |
| 5,149,329 A | 9/1992 | Richardson | |
| 5,259,835 A | 11/1993 | Clark et al. | |
| 5,362,294 A | 11/1994 | Seitzinger | |
| 5,386,836 A | 2/1995 | Biswas | |
| 5,434,146 A | 7/1995 | Labrie et al. | |
| 5,439,467 A | 8/1995 | Benderev et al. | |
| 5,456,711 A | 10/1995 | Hudson et al. | |
| 5,507,754 A | 4/1996 | Green et al. | |
| 5,522,896 A | 6/1996 | Prescott et al. | |
| 5,562,689 A | 10/1996 | Green et al. | |
| 5,569,273 A | 10/1996 | Titone et al. | |
| 5,611,515 A | 3/1997 | Benderev et al. | |
| 5,647,836 A | 7/1997 | Blake et al. | |
| 5,695,525 A | 12/1997 | Mulhauser et al. | |
| 5,697,931 A | 12/1997 | Thompson | |
| 5,749,884 A | 5/1998 | Benderev et al. | |
| 5,766,221 A | 6/1998 | Benderev et al. | |
| 5,816,258 A | 10/1998 | Jervis | |
| 5,840,011 A | 11/1998 | Landgrebe et al. | |
| 5,851,229 A | 12/1998 | Lentz et al. | |
| 5,904,692 A | 5/1999 | Steckel et al. | |
| 5,922,026 A | 7/1999 | Chin | |
| 5,934,283 A | 8/1999 | Willem et al. | |
| 5,954,057 A | 9/1999 | Li | |
| 6,010,447 A | 1/2000 | Kardjian | |
| 6,039,686 A | 3/2000 | Kovac | |
| 6,042,534 A | 3/2000 | Gellman et al. | |
| 6,042,536 A | 3/2000 | Tihon et al. | |
| 6,042,583 A | 3/2000 | Thompson et al. | |
| 6,048,306 A | 4/2000 | Spielberg | |
| 6,048,351 A | 4/2000 | Gordon et al. | |
| 6,050,937 A | 4/2000 | Benderev | |
| 6,053,935 A | 4/2000 | Brenneman et al. | |
| 6,056,688 A | 5/2000 | Benderev et al. | |
| 6,068,591 A | 5/2000 | Bruckner et al. | |
| 6,077,216 A | 6/2000 | Benderev et al. | |
| 6,090,116 A | 7/2000 | D'Aversa et al. | |
| 6,110,101 A | 8/2000 | Tihon et al. | |
| 6,117,067 A | 9/2000 | Gil-Vernet | |
| 6,162,962 A | 12/2000 | Hinsch et al. | |
| 6,197,036 B1 | 3/2001 | Tripp et al. | |
| 6,221,005 B1 | 4/2001 | Bruckner et al. | |
| 6,231,496 B1 | 5/2001 | Wilk et al. | |
| 6,245,082 B1 | 6/2001 | Gellman et al. | |
| 6,264,676 B1 | 7/2001 | Gellman et al. | |
| 6,267,772 B1 | 7/2001 | Mulhauser et al. | |
| 6,273,852 B1 | 8/2001 | Lehe et al. | |
| 6,287,316 B1 | 9/2001 | Agarwal et al. | |
| 6,306,079 B1 | 10/2001 | Trabucco | |
| 6,328,686 B1 | 12/2001 | Kovac | |
| 6,334,446 B1 | 1/2002 | Beyar | |
| 6,355,065 B1 | 3/2002 | Gabbay | |
| 6,387,041 B1 | 5/2002 | Harari et al. | |
| 6,406,423 B1 | 6/2002 | Scetbon | |
| 6,408,656 B1 | 6/2002 | Ory et al. | |
| 6,418,930 B1 | 7/2002 | Fowler | |
| 6,475,139 B1 | 11/2002 | Miller | |
| 6,478,791 B1 | 11/2002 | Carter et al. | |
| 6,491,703 B1 | 12/2002 | Ulmsten | |
| 6,527,802 B1 | 3/2003 | Mayer | |
| 6,544,273 B1 | 4/2003 | Harari et al. | |
| 6,575,897 B1 | 6/2003 | Ory et al. | |
| 6,596,001 B2 | 7/2003 | Stormby et al. | |
| 6,599,235 B2 | 7/2003 | Kovac | |
| 6,599,318 B1 | 7/2003 | Gabbay | |
| 6,599,323 B2 | 7/2003 | Melican et al. | |
| 6,638,210 B2 | 10/2003 | Berger | |
| 6,638,211 B2 | 10/2003 | Suslian et al. | |
| 6,638,284 B1 | 10/2003 | Rousseau et al. | |
| 6,641,524 B2 | 11/2003 | Kovac | |
| 6,652,450 B2 | 11/2003 | Neisz et al. | |
| 6,652,595 B1 | 11/2003 | Nicola | |
| 6,666,817 B2 | 12/2003 | Li | |
| 6,669,706 B2 | 12/2003 | Schmitt et al. | |
| 6,669,735 B1 | 12/2003 | Pelissier | |
| 6,673,010 B2 | 1/2004 | Skiba et al. | |
| 6,679,896 B2 | 1/2004 | Gellman et al. | |
| 6,689,047 B2 | 2/2004 | Gellman | |
| 6,691,711 B2 | 2/2004 | Raz et al. | |
| 6,695,855 B1 | 2/2004 | Gaston | |
| 6,702,827 B1 | 3/2004 | Lund et al. | |
| 6,960,160 B2 * | 11/2005 | Browning | 600/37 |
| 7,025,063 B2 | 4/2006 | Snitkin et al. | |
| 7,112,210 B2 | 9/2006 | Ulmsten et al. | |
| 7,156,858 B2 | 1/2007 | Schuldt-Hempe et al. | |
| 2001/0018549 A1 | 8/2001 | Scetbon | |
| 2001/0049538 A1 | 12/2001 | Trabucci | |
| 2001/0053916 A1 | 12/2001 | Rioux | |
| 2002/0005204 A1 | 1/2002 | Benderev et al. | |
| 2002/0042658 A1 | 4/2002 | Tyagi | |
| 2002/0049503 A1 | 4/2002 | Milbocker | |
| 2002/0052612 A1 | 5/2002 | Schmitt | |
| 2002/0052654 A1 | 5/2002 | Darois et al. | |
| 2002/0077526 A1 | 6/2002 | Kammerer et al. | |
| 2002/0083949 A1 | 7/2002 | James | |
| 2002/0099260 A1 | 7/2002 | Suslian et al. | |
| 2002/0138025 A1 | 9/2002 | Gellman et al. | |
| 2003/0023137 A1 | 1/2003 | Gellman | |
| 2003/0199732 A1 | 10/2003 | Suslian et al. | |
| 2004/0029478 A1 | 2/2004 | Planck et al. | |
| 2004/0034373 A1 | 2/2004 | Schuldt-Hempe et al. | |
| 2004/0172048 A1 | 9/2004 | Browning | |
| 2004/0249373 A1 | 12/2004 | Gronemeyer et al. | |
| 2004/0249397 A1 | 12/2004 | Delorme et al. | |
| 2004/0249473 A1 | 12/2004 | Delmore et al. | |
| 2005/0000524 A1 | 1/2005 | Cancel et al. | |
| 2006/0041185 A1 | 2/2006 | Browning | |
| 2006/0058578 A1 | 3/2006 | Browning | |
| 2006/0205995 A1 | 9/2006 | Browning | |
| 2007/0020311 A1 | 1/2007 | Browning | |
| 2007/0032881 A1 | 2/2007 | Browning | |

FOREIGN PATENT DOCUMENTS

| | | |
|---|---|---|
| EP | 0009072 B1 | 4/1980 |
| EP | 0024780 B1 | 3/1981 |
| EP | 0024781 B1 | 3/1981 |
| EP | 0139286 B1 | 5/1981 |
| EP | 0 248 544 A | 12/1987 |
| EP | 0557964 B1 | 9/1993 |
| EP | 0 632 999 A | 1/1995 |
| EP | 0706778 B1 | 4/1996 |
| EP | 0719527 B1 | 7/1996 |
| EP | 0797962 B1 | 10/1997 |
| EP | 1060714 B1 | 12/2000 |
| FR | 2712177 B1 | 5/1995 |
| FR | 2732582 B1 | 10/1996 |
| FR | 2735015 B1 | 12/1996 |
| FR | 2 787 990 A1 | 7/2000 |
| FR | 1274370 B2 | 9/2006 |
| WO | WO9100714 B1 | 1/1991 |
| WO | WO9533454 B1 | 12/1995 |
| WO | WO9603091 B1 | 2/1996 |
| WO | WO 96/06567 A1 | 3/1996 |
| WO | WO 97/13465 A1 | 4/1997 |
| WO | WO9722310 B1 | 6/1997 |
| WO | WO 98/35632 A1 | 8/1998 |
| WO | WO9857590 B1 | 12/1998 |
| WO | WO9916381 B1 | 4/1999 |
| WO | WO 99/59477 A1 | 11/1999 |

| | | | |
|---|---|---|---|
| WO | WO0007520 B1 | 2/2000 |
| WO | WO0015141 B1 | 3/2000 |
| WO | WO0038784 B1 | 7/2000 |
| WO | WO 00 74633 A | 12/2000 |
| WO | WO0180773 B2 | 11/2001 |
| WO | WO 02 30293 A | 4/2002 |
| WO | WO02060371 B2 | 8/2002 |
| WO | WO02065944 B2 | 8/2002 |
| WO | WO 02 078571 A | 10/2002 |
| WO | WO02078568 B2 | 10/2002 |
| WO | WO 02/098340 A1 | 12/2002 |
| WO | WO 03 002027 A | 1/2003 |
| WO | WO 03/013392 A1 | 2/2003 |
| WO | WO03022260 B2 | 3/2003 |
| WO | WO03057074 B2 | 7/2003 |
| WO | WO03086205 B2 | 10/2003 |
| WO | WO03092546 B2 | 11/2003 |
| WO | WO03094781 B2 | 11/2003 |
| WO | 2004004600 B2 | 1/2004 |
| WO | 2004012626 B2 | 2/2004 |
| WO | 2004002379 B2 | 11/2004 |
| WO | 2004098461 B2 | 11/2004 |
| WO | 2005018494 B2 | 3/2005 |
| WO | 2008018494 B2 | 1/2008 |

OTHER PUBLICATIONS

U.S. Appl. No. 60/302,929, filed Jul. 2001, Lund et al.
U.S. Appl. No. 60/307,836, filed Jul. 2001, Neisz et al.
U.S. Appl. No. 60/322,309, filed Sep. 2001, Kimberly Anderson et al.
U.S. Appl. No. 10/106,086, filed Mar. 2002, Neisz et al.

DeBord, James R., (1998). "The Historical Development of Prosthetics in Hernia Survery," Surgical Clinics of North America, 78(6):973-1006.
Klinge, U. et al., (1996), "Pathophysiology of the abdominal wall," Der Chirurgm 67:229-233.
Klinge, U. et al (1998). "Modified Mesh for Hernia Repair that is Adapted to the Physiology of the Abdominal Wall," Eir J Surg, 164:951-960.
Klinge, U. et al., (1999), "Influence of polyglactin-coating on functional and morphological parameters of polypropylene-mesh modifications for abdominal wall repair," Biomaterials, 20:613-623.
Klinge et al., (2002), "Function and Morphological Evaluation of a Low-Weight, Monofilament Polypropylene Mesh for Hernia Repair," Journal of Biomedical Materials Research, 63(2):129-137.
Klosterhalfen, B. et al, (1997), "Morphological correlation of the functional mechanics of the abdominal wall after mesh implantation," Langenbecks Arch Chir, 382:87-94.
Klosterhalfen, B, et al., (1998), "Functional and morphological evaluation of different polypropylene-mesh modifications for abdominal wall repair," Biomaterials 19:2235-2246.
Lipton, S. and Estrin, J., (1994), "A Biomechanical Study of the Aponeurotic Iguinal Hernia Repair," Journal of the American College of Surgeons, vol. 178, pp. 595-599.
Nicita, Giulio, (1998), "A New Operation for Genitourinary Prolapse," The Journal of Urology, 160:741-745.
Schumpelick, v. et al., (1999), "Minimized polypropylene mesh for preperitoneal net plasty (PNP) of incisional hernias," Chirug 70:422-430.

* cited by examiner

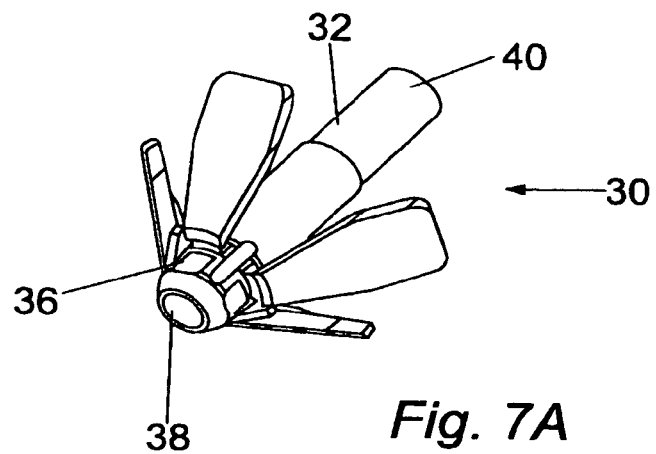
Fig. 7A
Fig. 7B
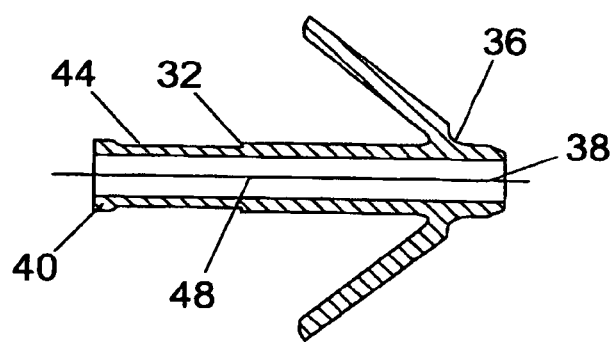
Fig. 7C
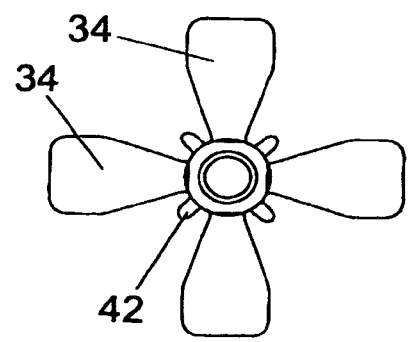

APPARATUS AND METHOD FOR TREATING FEMALE URINARY INCONTINENCE

CROSS REFERENCE TO RELATED APPLICATIONS

This application is a continuation of U.S. patent application Ser. No. 10/398,992, filed Apr. 11, 2003, issued as U.S. Pat. No. 6,960,160 on Nov. 1, 2005, which claims priority to international patent application PCT/GB01/04554, filed Oct. 12, 2001, and GB0025068.8, filed Oct. 12, 2000, the contents of each of which are incorporated by reference herein.

This invention relates to an apparatus and method for treating female urinary incontinence and, in particular, to a surgical implant having a sling that passes under the urethra in use and supports the urethra to alleviate incontinence, along with related apparatus and methods for inserting the surgical implant in the body.

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey-type endoscopic procedures in which the sutures are placed so as to elevate the bladder neck.

This invention is particularly directed to improvement of a known procedure in which a sling is positioned loosely under the urethra, commonly known as TVT (tension free vaginal tape) and described, for example, in International Patent Applications No. WO97/13465 and WO97/06567. It is generally understood that this treatment alleviates urinary incontinence by occluding the mid-urethra (for example at a time of raised abdominal pressure by coughing or the like).

The sling is provided in the body using two large curved needles which are provided at each end of the sling, which sling comprises a long mesh or tape. Each of the needles is carried on an insertion tool (which is basically a handle facilitating manipulation of the needles). The mesh or tape is usually made of knitted polypropylene (such as Prolene®). The mesh or tape is generally covered with a plastics sleeve or polythene envelope to aid smooth insertion, the mesh or tape having rough surfaces to aid retention in the body.

An incision is made in the anterior vaginal wall and the first of the needles is passed through the incision, past one side of the urethra, behind the pubic bone, through the rectus sheath and out through the lower anterior abdominal wall. Likewise, the second needle is passed through the incision, past the other side of the urethra, behind the pubic bone, through the rectus sheath and out through the lower abdominal wall. The needles are separated from their respective insertion tools and also from the mesh or tape such that only the tape and its plastics sleeve are left in the body, passing from a first exit point in the lower abdominal wall, through the rectus sheath, behind the pubic bone, under the urethra, back behind the pubic bone, back through the rectus sheath and out through a second exit point in the lower abdominal wall.

The plastics sleeve is then removed from the tape and the tape adjusted to a suitable tension (such that the tape provides a sling that passes loosely under the urethra, as described above) by maneuvering the free ends of the tape outside the exit points in the lower abdominal wall whilst the urethra is held using a rigid catheter inserted therein. The tape is then cut such that it just falls short of protruding from the exit points in the lower abdominal wall. The exit points and the incision in the upper vaginal wall are then closed by sutures. The tape is held in position by virtue of friction between the tape's rough edges and the surrounding body tissue (such as the rectus sheath and the body tissue behind the pubic bone) and subsequent natural adhesion of the tape with the body tissue as it re-grows around the mesh material. Whilst highly effective in treating urinary incontinence, this procedure has a number of problems. One such problem is that the needles used for inserting the tape are comparatively large, with the needles having, for example, a diameter of around 5-6 mm and a length of around 200 mm. As well as causing concern for patients viewing such needles before or during the procedure (which is carried out under local anaesthetic), this can also lead to a high vascular injury rate.

Similarly, the requirement that the needles exit the lower abdominal wall is disadvantageous due to the trauma to the patient in this area and pain of such abdominal wounds. A further disadvantage is that the tape comprises a relatively large foreign body mass to be retained within the patient and this can lead to related inflammation, infection translocation, erosion, fistula and such like.

Similarly, the nature of the large needles and tape, along with the tools required to insert these in the body, lead to the procedure having a relatively high cost.

According to a first aspect of the present invention there is provided a surgical implant for supporting the urethra, the implant comprising: a suburethral support suspended between at least two soft tissue anchors attached at either side of the suburethral support, each soft tissue anchor having retaining means for retaining each anchor in tissue and suspending means for suspending each side of the suburethral support from a soft tissue anchor such that the suburethral support passes under the urethra in use.

Preferably the retaining means of the soft tissue anchor is capable of being inserted into soft tissue or fascia from an incision in the upper vaginal wall without the need to penetrate the lower abdominal wall.

In one embodiment the soft tissue anchor is insertable into the rectus sheath of the human or animal body to anchor suspending means to the soft tissue, the suspending means being attached to the soft tissue anchor and the soft tissue anchor having retaining means adapted to prevent retraction of the anchor from the rectus sheath in a direction opposite to that of insertion of the anchor into the tissue.

Preferably the soft tissue anchor comprises a central portion and the retaining means includes at least one wing section, the wing section being mounted on a first end of the central portion by resilient hinge means such that the wing section is moveable between an open, resting position and a deflected position such that in use, when the soft tissue anchor device is inserted into the tissue the wing section is pushed or held towards the central portion to a deflected position to permit entry of the soft tissue anchor into the tissue and through the rectus sheath, wherein the wing section returns to its open or resting position and prevents the soft tissue being removed.

Preferably the resilient hinge means allows the wing section to return to its resting position from its deflected position following penetration of the soft tissue anchor through the rectus sheath such that the wings of the soft tissue anchor once pushed through the rectus sheath can rest on the surface of the rectus sheath fascia opposite to the surface through which the soft tissue anchor is inserted and thus the soft tissue anchor cannot be retracted.

Preferably the resilient hinge means is capable of preventing the wing section being moved to a position greater than substantially perpendicular to the central portion.

Preferably the central portion of the soft tissue anchor comprises a hollow passage which extends from a first end of the central portion to a second opposite end of the central portion.

Preferably an introducing tool can be placed into the hollow passage such that the introducing tool extends through the central portion the soft tissue anchor such that the introducing tool extends to a point beyond the first end of the central portion.

Preferably the soft tissue anchor comprises a plurality of wing sections.

More preferably the soft tissue anchor comprises four wing sections arranged radially around the first end of the central portion.

Preferably the soft tissue anchor in addition to comprising a central portion and a wing section also comprises at least one stud element arranged radially around the first end of the central portion, the stud having an inclined face in the opposite direction to that in which the soft tissue anchor is inserted to aid separation of the tissue during entry of the soft tissue anchor enabling easier passage of the soft tissue anchor through the soft tissue.

Preferably the soft tissue anchor does not comprise a sharp point.

In an alternative embodiment the soft tissue anchor is capable of anchoring in the retropubic tissue space without penetrating the rectus sheath.

Preferably the soft tissue anchor in this embodiment permits fixation at multiple points via a Christmas tree type configuration of deflectable wings.

A soft tissue anchor according to this embodiment comprises a central portion and the retaining means includes a plurality of projections the projections extending radially from the central portion along a substantial portion of the length of the central portion allowing fixation at a plurality of layers. Preferably the projections extend radially from the central portion at an angle inclined toward the second end of the central portion.

Preferably the projections are of a shape that they are able to provide additive traction to the soft tissue anchor and allow it to grip fibro-fatty soft tissue and blood vessels of the paraurethral tunnel below the level of the rectus sheath.

In yet a further embodiment the soft tissue anchor may comprise a substantially flat head the bottom surface nearest the suspending means of the flat head providing the retaining means which, in use is held in the rectus sheath.

In a further embodiment the soft tissue anchor may comprise a sharp point allowing it to pierce or penetrate the rectus sheath, and retaining means comprising a surface or protrusion directed rearwardly with respect to the sharp point which does not cause the soft tissue to part and thus prevents the soft tissue anchor from being pulled back out through the rectus sheath soft tissue in the direction opposite to that in which it is inserted into the soft tissue.

Preferably the sharp point is provided by the apex of a conical head portion and retaining means are provided by a substantially flat base of the conical head.

In any embodiment the soft tissue anchor is comprised of plastics material.

Typically the soft tissue anchor is comprised of polypropylene.

Alternatively the soft tissue anchor is comprised of absorbable material so as to form temporary fixation in soft tissue.

The soft tissue anchor may comprise a point formed of absorbable material including polyglactin, the sharp point thus capable of facilitating insertion of the anchor, yet being absorbed by the body later.

Preferably the soft tissue anchor may be integral with the suspending means.

More preferably the soft tissue anchor is integrally formed from polypropylene or other polymeric material the attachment between the anchor and the suspending being formed as a single unit.

An integral construction of the soft tissue anchor and suspending means has the advantage of simplifying the construction of the soft tissue anchor and suspending means, which can reduce the possibility of defective manufacture etc. and reduce costs and the chance of the soft tissue anchor and suspending means becoming detached once implanted in the body.

Alternatively the soft tissue anchor is attached to the suspending means by a thin metal tube crimped or otherwise attached around the suspending means and central portion of the soft tissue anchor.

The suburethral support of the first aspect of the invention passes under the urethra, loosely supporting the urethra, the suburethral support being held in position by suspending means attached to each of its free ends on either side of the urethra, the suspending means being attached at the opposite end to at least one soft tissue anchor.

Preferably the suburethral support is comprised of flat polymer tape.

Preferably the suburethral support has dimensions sufficient only to pass around the urethra.

More preferably the suburethral support has dimensions of length 15-35 mm, width 5-15 mm and thickness 50-350 µm.

In one embodiment the suburethral support has dimensions of length 25 mm, width 10 mm and thickness 100 µm.

Preferably the suburethral support has at least two junctions to attach the suburethral support to the suspending means.

One problem with the preferred arrangement of a soft tissue anchor and suspending means for suspending the suburethral support of the surgical implant of the invention is that it is difficult to predetermine what length the suspending means must be to position the suburethral support loosely under the urethra as desired.

This is because the distance between the rectus sheath in which the soft tissue anchor is inserted and the urethra varies from patient to patient.

Preferably the distance between the soft tissue anchor(s) and the suburethral support is adjustable.

More preferably the soft tissue anchor (or anchors) can be positioned first and the suburethral support then positioned by adjusting the length of the suspending means.

Preferably the suburethral support is provided with at least one attachment tab to which suspending means are releasably or permanently attached.

Preferably the suburethral support comprises an attachment tab comprising a tunnelled element and an aperture, the tunnelled element being located at each of the free ends of the suburethral support on either side of the urethra at a position that the suspending means are capable of being introduced through, the tunnelled element co-operating with the aperture such that suspending means can be passed through the tunnelled element and then through the aperture, the aperture being present on the opposite surface of the suburethral support to that which contacts the urethra the aperture having an edge capable of co-operating with a ring element and the ring element being capable of being fitted around the aperture trapping the suspending means between the ring element and the edge of the aperture such that the suspending means remain fixed in an adjusted position wherein the suburethra support hanging loosely under the urethra.

Alternatively the attachment tab comprises at least one slot through which suspending means can be passed, the suspending means being permanently attached to the slot by tying.

Alternatively the attachment tab comprises jamming slots that the suspending means can be permanently attached by being threaded through the jamming slots such that the suspending means are held in an adjusted position.

Alternatively the suburethral support is capable of being suitably positioned under the urethra by altering the position of the soft tissue anchors within the body such that at least one soft tissue anchor is secured in the soft tissue or in the rectus sheath and a subsequent anchor is inserted into the soft tissue or rectus sheath to a suitable depth such that the suburethral support hangs loosely under the urethra.

Alternatively the suspending means may be attached to the suburethral support by healing such that the suburethra support and/or suspending means melt and form a join.

Alternatively the attachment tabs may have closure means for gripping the suspending means.

The suspending means may be any means suitable for connecting each end of the suburethra support to the soft tissue anchor (or respective soft tissue anchors).

Preferably the suspending means comprises a plastics strip.

Preferably the plastics strip has smooth edges.

Preferably the plastics strip comprises material such as polypropylene or other suitable non-absorbable or absorbable polymer tape.

Preferably the plastics strip is 3-5 mm in width.

Preferably the plastics material comprises pores which extend through the plastics material from a first surface of the plastics material to a second opposite surface of the plastics material said pores ranging in width across the surface of the plastics material from 50 μm to 200 μm, the pores allowing tissue in-growth to secure the strip in the body.

Alternatively the plastics material may comprise pits, that indent but do not extend through the plastics material, on at least one of the surfaces of the plastics material, the pits ranging in width from 50 μm to 200 μm, the pits allowing tissue in-growth to secure the strip in the body.

Preferably the plastics material comprises pits or pores ranging in width across the surface of the plastics material from 100 μm to 150 μm.

Preferably the pits or pores are distributed across the complete surface of the plastics material.

Alternatively the pits or pores are distributed only in a particular portion of the surface of the plastics material.

Preferably the pits or pores are created by post synthesis modification of the plastics material.

More preferably the pits or pores are created by post synthesis treatment of the plastics material by a laser.

Alternatively the pits or pores of between 50-200 μm are created during synthesis of the plastics material by spaces between the waft and weave of mono-filament or multi-filament yarns when the filaments are woven to form a mesh.

Alternatively pits or pores formed during the synthesis of plastics material are formed by the inter-filament spaces created when mono-filaments are twisted to create multi-filaments, the multi-filaments then being woven to form a mesh.

In an embodiment the suspending means is provided with a plurality of microgrooves of width between 0.5-7 μm and of depth 0.25-7 μm on at least one surface of the plastics strip.

Preferably the microgrooves are 5 μm in width and 5 μm in depth.

Preferably the plurality of microgrooves are aligned such that they are substantially parallel with each other.

Preferably the plurality of microgrooves are aligned such that they are separated by ridges which range in size between 1-5 μm in width.

More preferably the microgrooves are separated by ridges of 5 μm in width.

Preferably the ridges are formed by square pillars and the base of the microgroove is substantially perpendicular to the square pillars.

Alternatively the ridges are formed by square pillars and the base of the microgroove is bevelled in relation to the pillars.

Preferably the microgrooves are present on at least one surface of the suspending means.

More preferably the microgrooves are present on a plurality of surfaces of the suspending means.

These microgrooves act to orientate and align the proliferating fibroblasts on the surface of the plastics material and cause axial alignment of collagen fibres and formation of at least one strong ordered neoligament.

The orientation and alignment of the proliferating cells is capable of adding mechanical strength to the tissue which forms around the plastics material such that it is more able to support the urethra.

Preferably the suburethral support of the present invention has neither pores, pits or grooves to discourage the formation of peri-urethral adhesions.

According to a second aspect of the present invention there is provided a method of supporting the urethra comprising the steps of, introducing a surgical implant as described above into an incision made on the upper wall of the vagina, inserting a soft tissue anchor on a first side of the urethra behind the pubic bone, inserting a second soft tissue anchor on a second side of the urethra behind the pubic bone, such that the suburethral support is suspended from the soft tissue anchor supports the urethra.

The invention also provides the use of the method of supporting the urethra in treating urinary incontinence or uterovaginal prolapse.

In one embodiment of the method the soft tissue anchors are inserted in the rectus sheath.

In an alternative embodiment of the method the soft tissue anchors are inserted in the fibro-fatty soft tissue of the retropubic tissue space and do not penetrate the rectus sheath.

The invention also provides an introducing tool comprising an elongate housing adapted to receive the soft tissue anchor at one end and a point which is capable of extending through the central portion of a soft tissue anchor for use in carrying out the method of the invention such that the introducing tool enables access and placement of the soft tissue anchor through the rectus sheath or in the fibrous fatty soft tissue of the para-urethral tunnel from an insertion point in the upper vaginal wall.

More preferably the elongate housing is curved or bent, preferably through an angle of approximately 30°.

It is desirable such that a sharp point of an anchor not is not retained in the body that the soft tissue anchor may be inserted using an introducing tool the introducing tool having a sharp point for penetrating the soft tissue.

Preferably an introducing tool comprises a sharp point for piercing or penetrating soft tissue and carrying means for carrying the soft tissue anchor to insert the anchor into the tissue such that the soft tissue anchor device does not require a sharp head and no sharp point is left in the body.

The overall size of the soft tissue anchor and introducing tool may be significantly smaller than that of the needles of the prior art.

Preferably the introducing tool may have a diameter of around 2 mm to 4 mm.

Preferably if the introducing tool is to be used in co-operation with a soft tissue anchor comprising a plurality of projections extending radially from the central portion along a substantial portion of the length of the central portion of the soft tissue anchor, the introducing tool comprises containment means for radially confining the plurality of projections extending from the central portion of the soft tissue anchor during the insertion of the soft tissue anchor.

Thus, when the soft tissue anchor has been inserted, the tool may release the retaining means around the soft tissue anchor such that the projections which have memory are biased to expand radially and grip the soft tissue.

The reduced size of the introducing tool in comparison to the needles used to introduce devices of the prior art can significantly reduce the vascular injury rate and perceptual problems of the prior art for a patient.

Preferably the introducing tool is able or has means for releasably retaining the soft tissue anchor on the end of the housing.

During the insertion of a surgical implant to support the urethra there is a risk of penetration of the bladder wall by the needles during insertion of the tape.

This is known to be a problem with the TVT procedure described by the prior art where the needles are inserted through an incision in the vagina to thread the tape through the respective punctures in the lower anterior abdominal wall.

Following the TVT procedure of the prior art it is therefore conventional to carry out cystoscopy after the tape has been inserted in the body to determine whether or not the bladder has been perforated. This is painful for the patient and also increases the duration of the operation.

The reduced size of the tools used for inserting the surgical implant of the present invention reduce to some degree the risk of the bladder being perforated during the surgical procedure, however it is nevertheless desirable to reduce the need for cystoscopy.

Accordingly at least a part of the surgical implant of the present invention may be coated or impregnated with a water soluble dye.

Preferably the soft tissue anchor of the present invention is impregnated with a water soluble dye.

Preferably, the water soluble dye is methylene blue.

It is possible to determine whether or not the bladder of a patient has been perforated by a surgical implant or instrument when inserting the surgical implant of the invention into the body, by expelling a small amount of fluid from the bladder, and determining whether or not this small amount of fluid contains any dissolved dye.

Should the bladder be perforated on insertion and placement of the surgical implant into the body, the dye impregnated into the surgical implant will dissolve in the fluid contained in the bladder and diffuse naturally throughout the fluid.

Thus should dye be present in the fluid, it is very likely that the bladder has been perforated and cystoscopy should be carried out. If there is no dye in the fluid, the bladder has not been perforated and the need for cystoscopy is obviated.

The soft tissue anchors as described in relation to the implant of the present invention are capable of use in a variety of situations.

Accordingly the invention provides soft tissue anchors as described herein.

The invention also provides the use of the soft tissue anchors in hernia repair, face lifts, plastic surgery and cosmetic surgery.

Figure 2A:
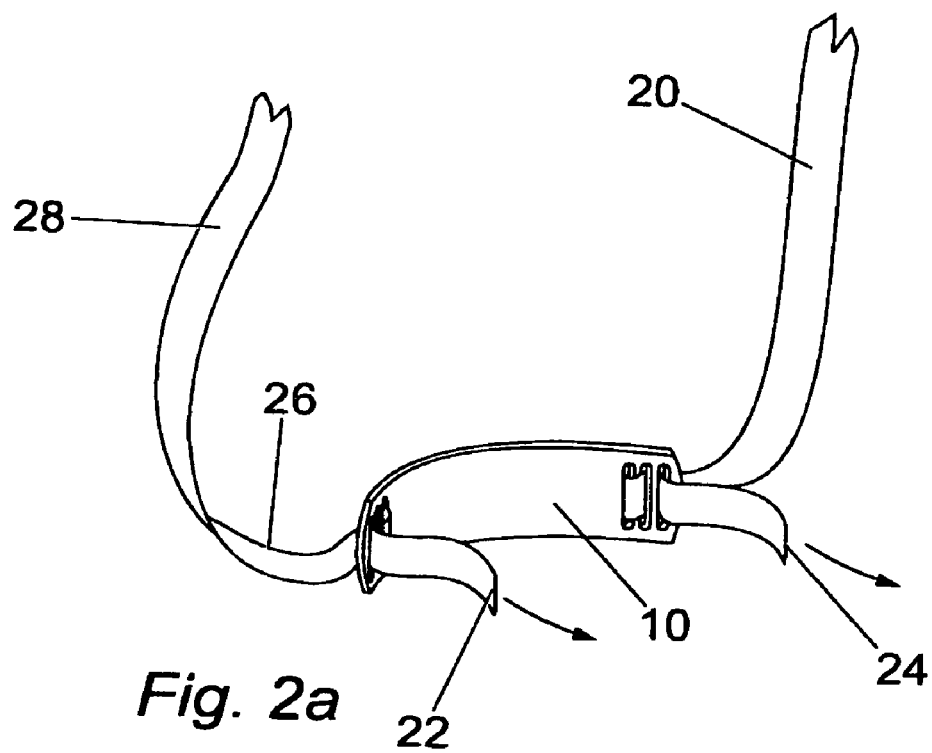
Figure 2B:
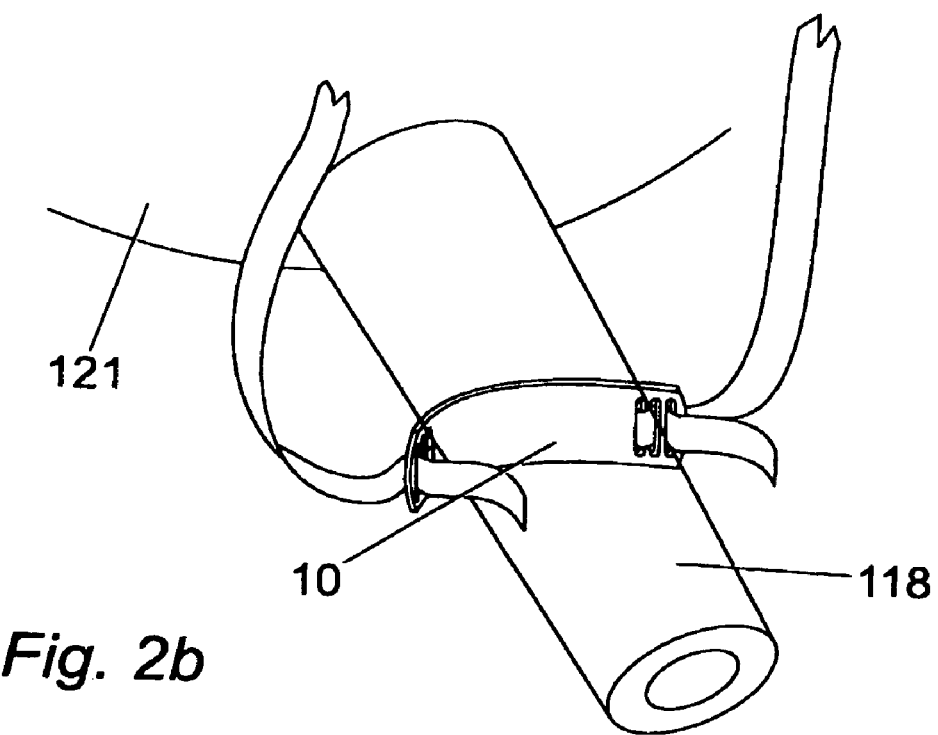
Figure 3:
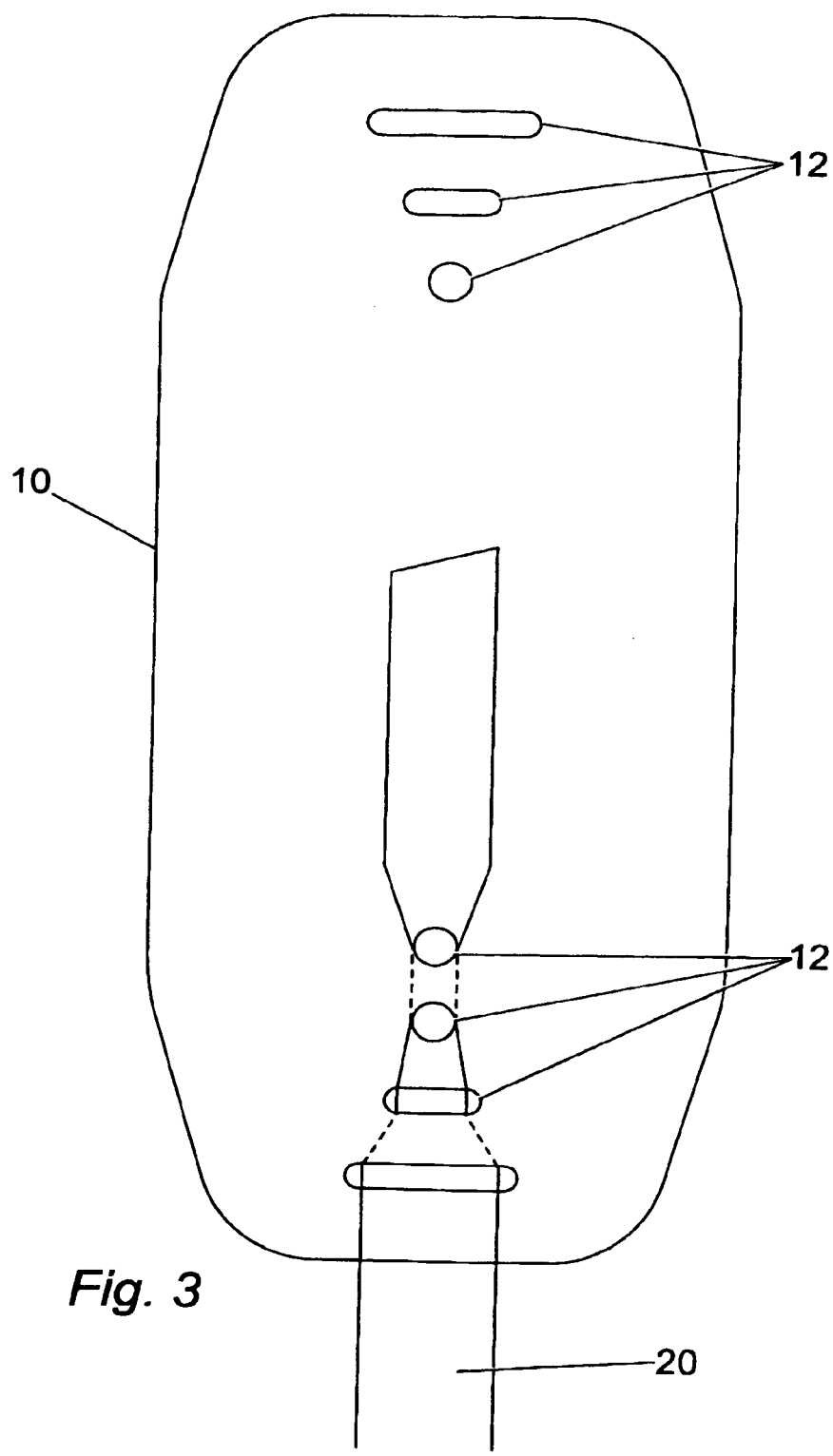
Figure 4:
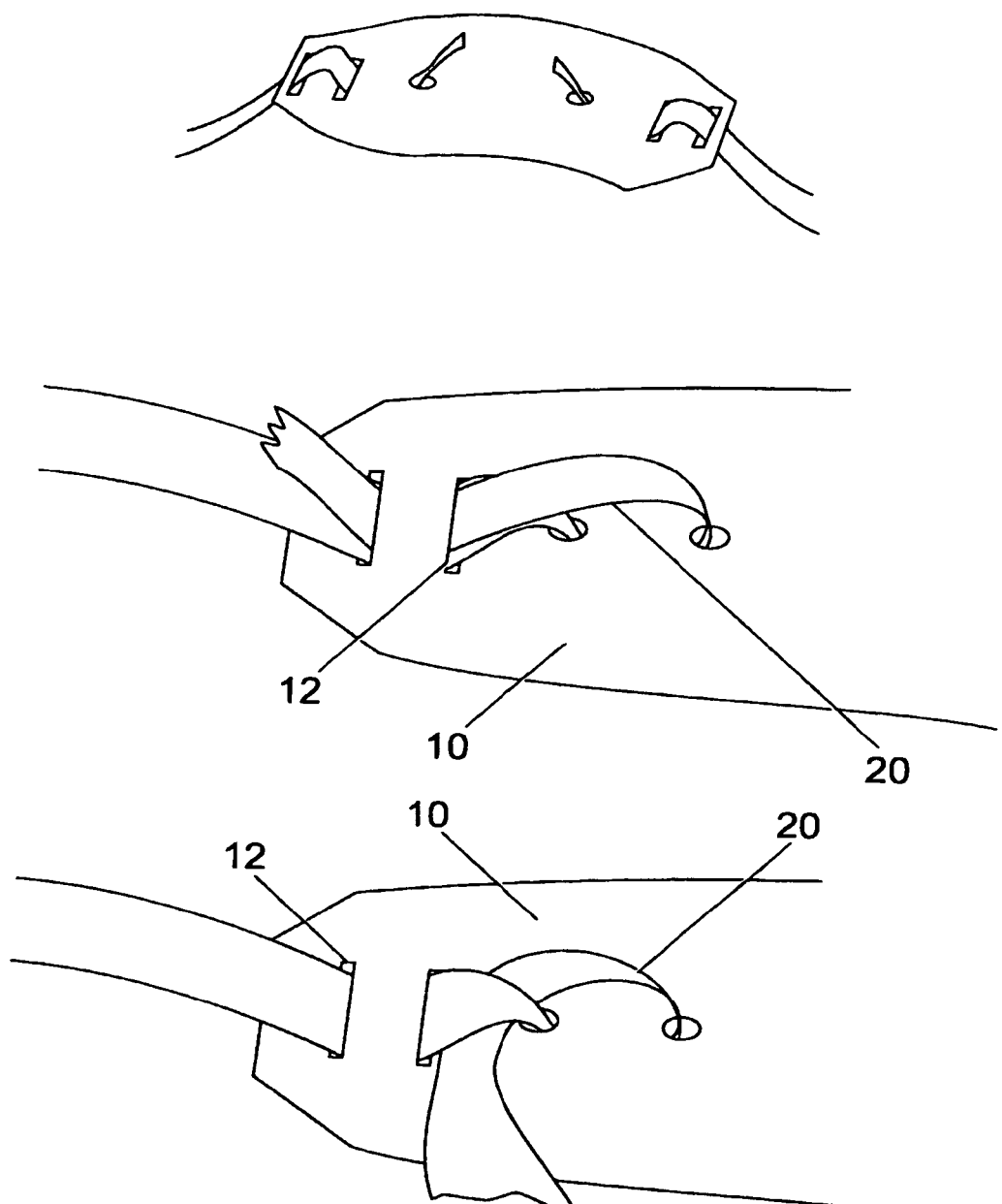
Figure 5:
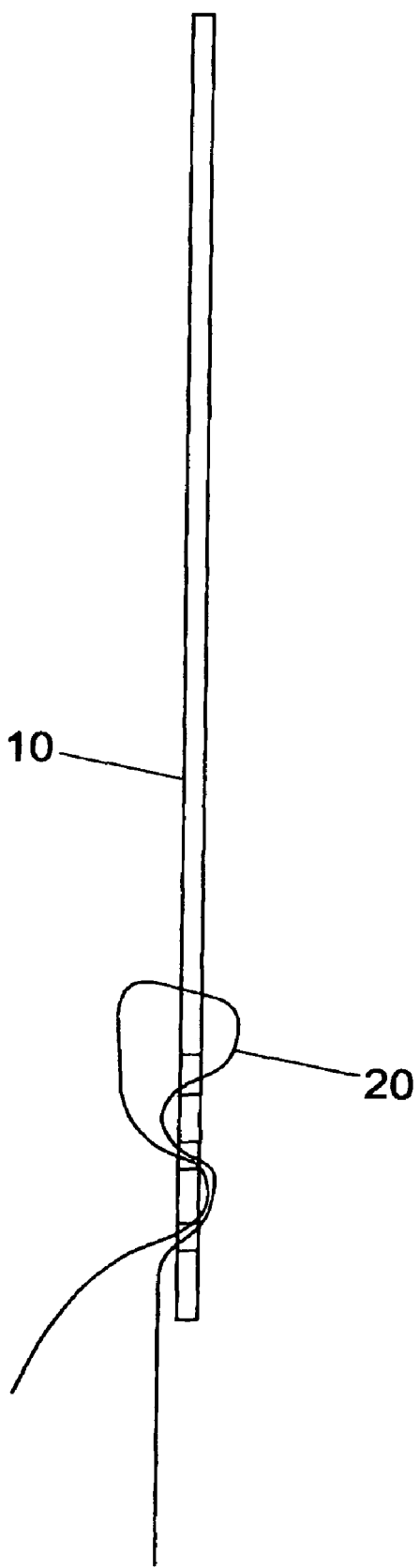
Figure 6A:
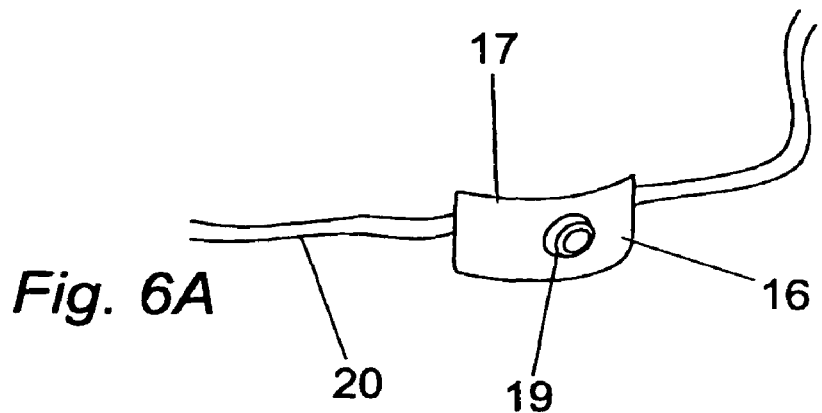
Figure 8A:
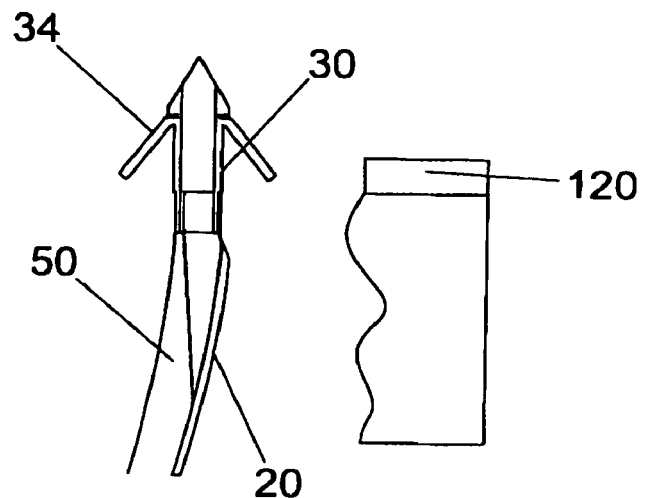
Figure 8B:
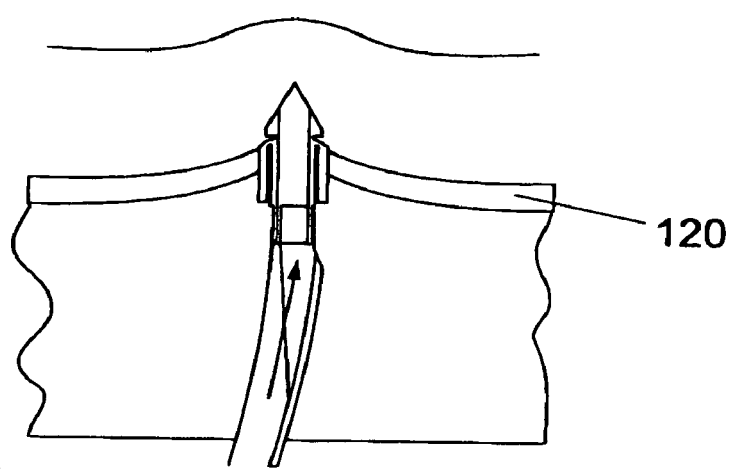
Figure 8C:
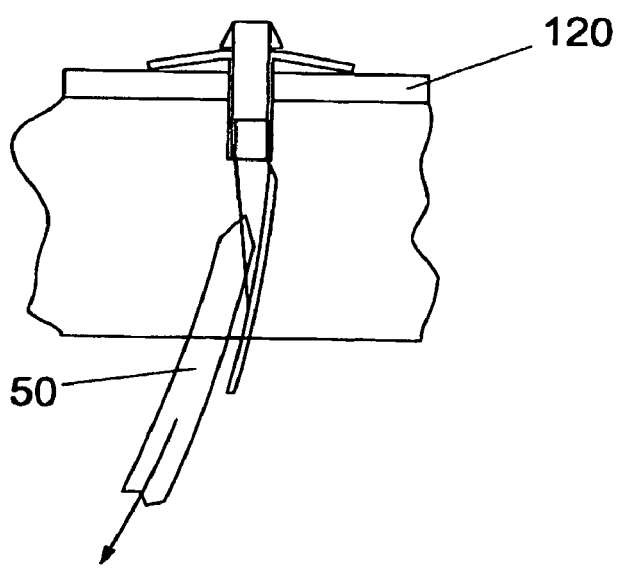
Figure 9:
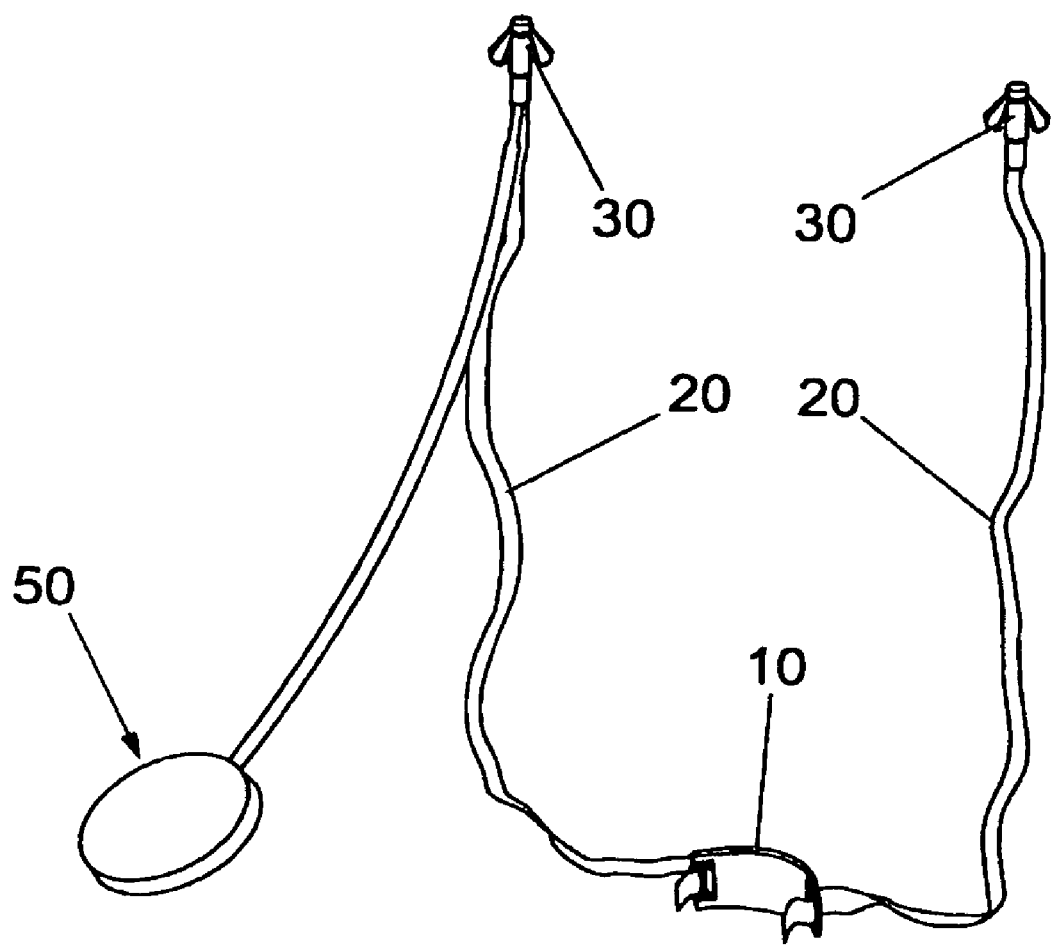
Figure 10:
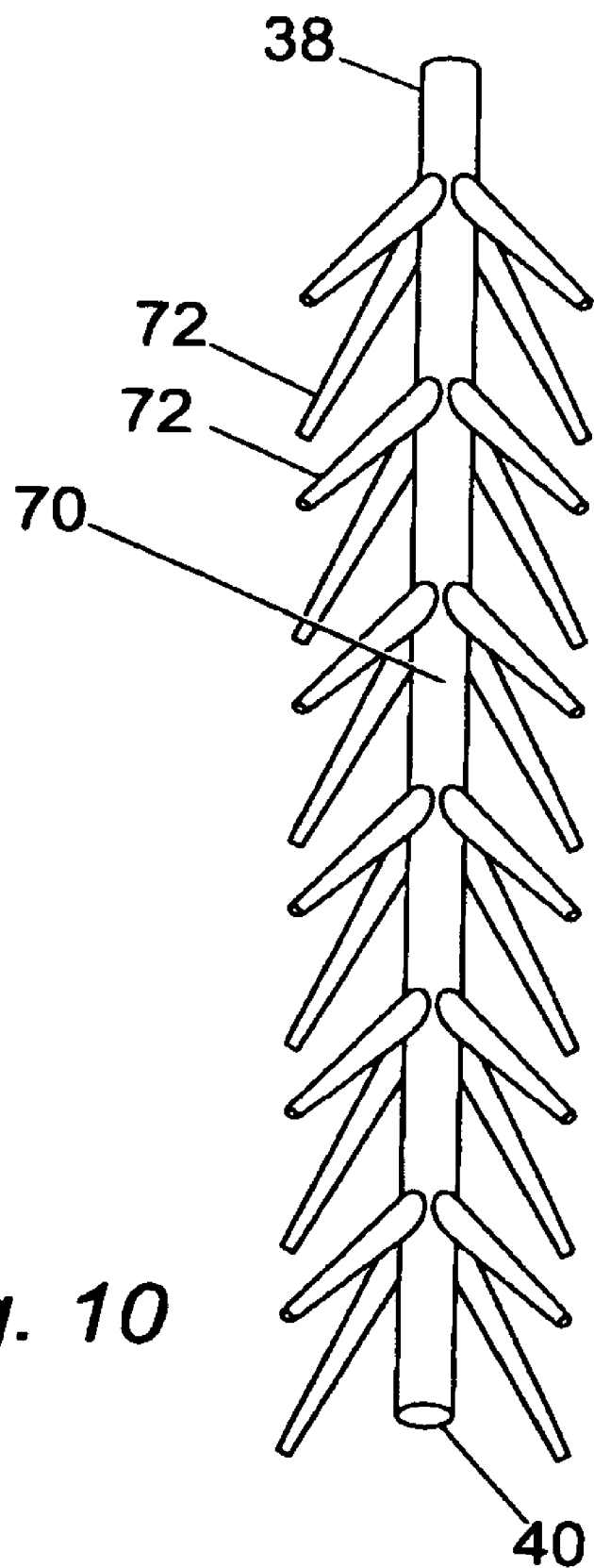
Figure 11:
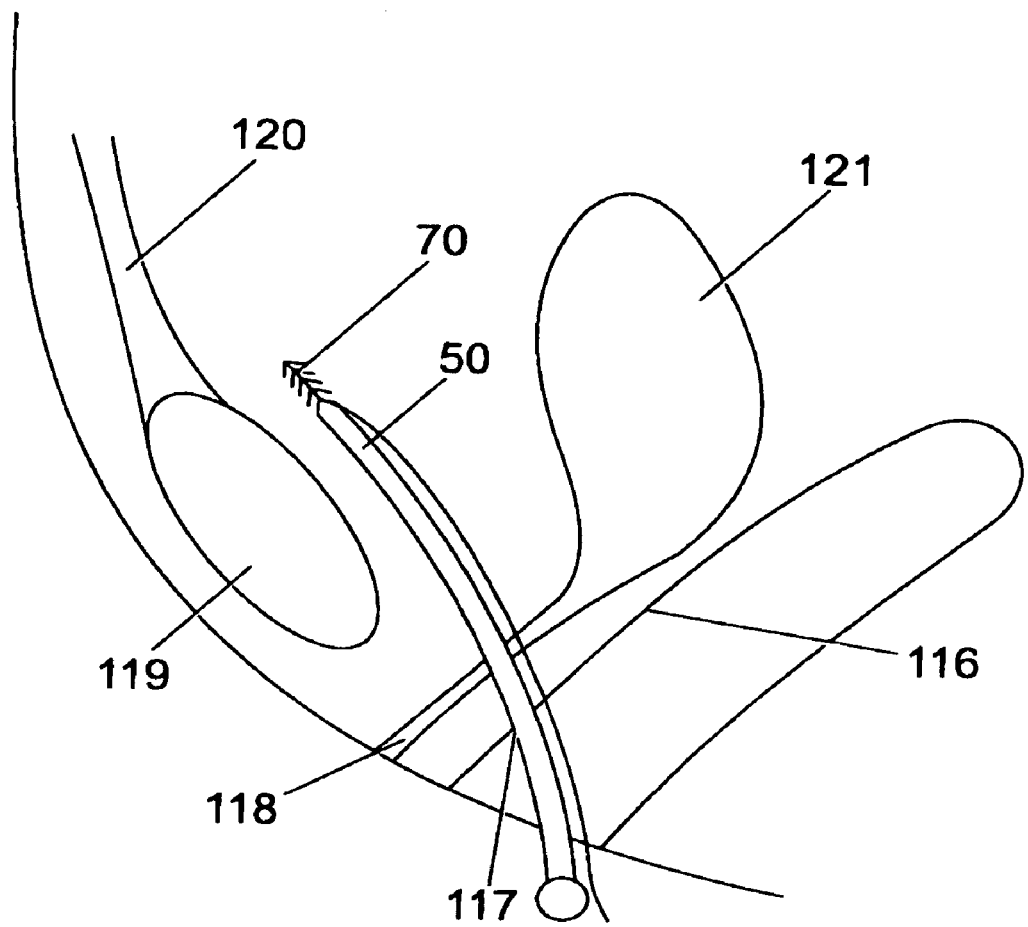
Figure 12:
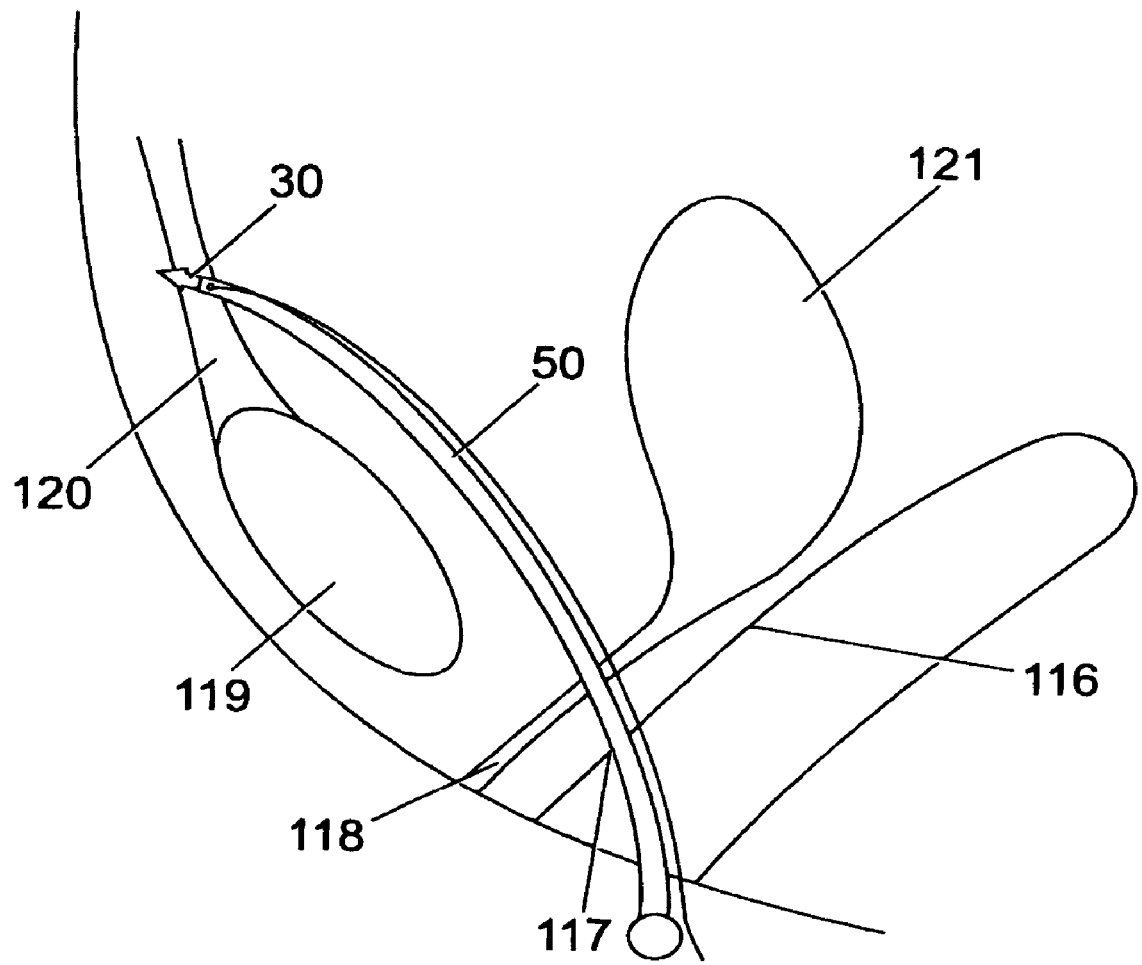
Figure 13:
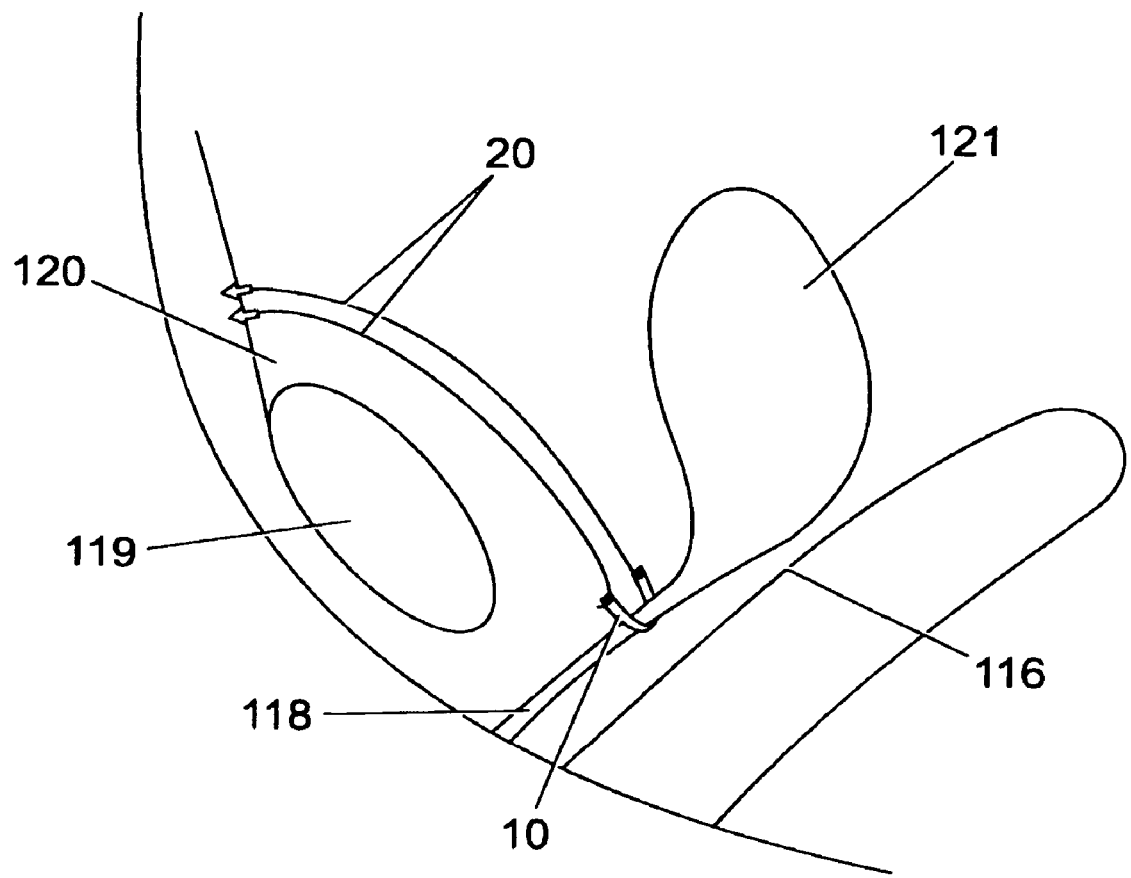
Figure 14:
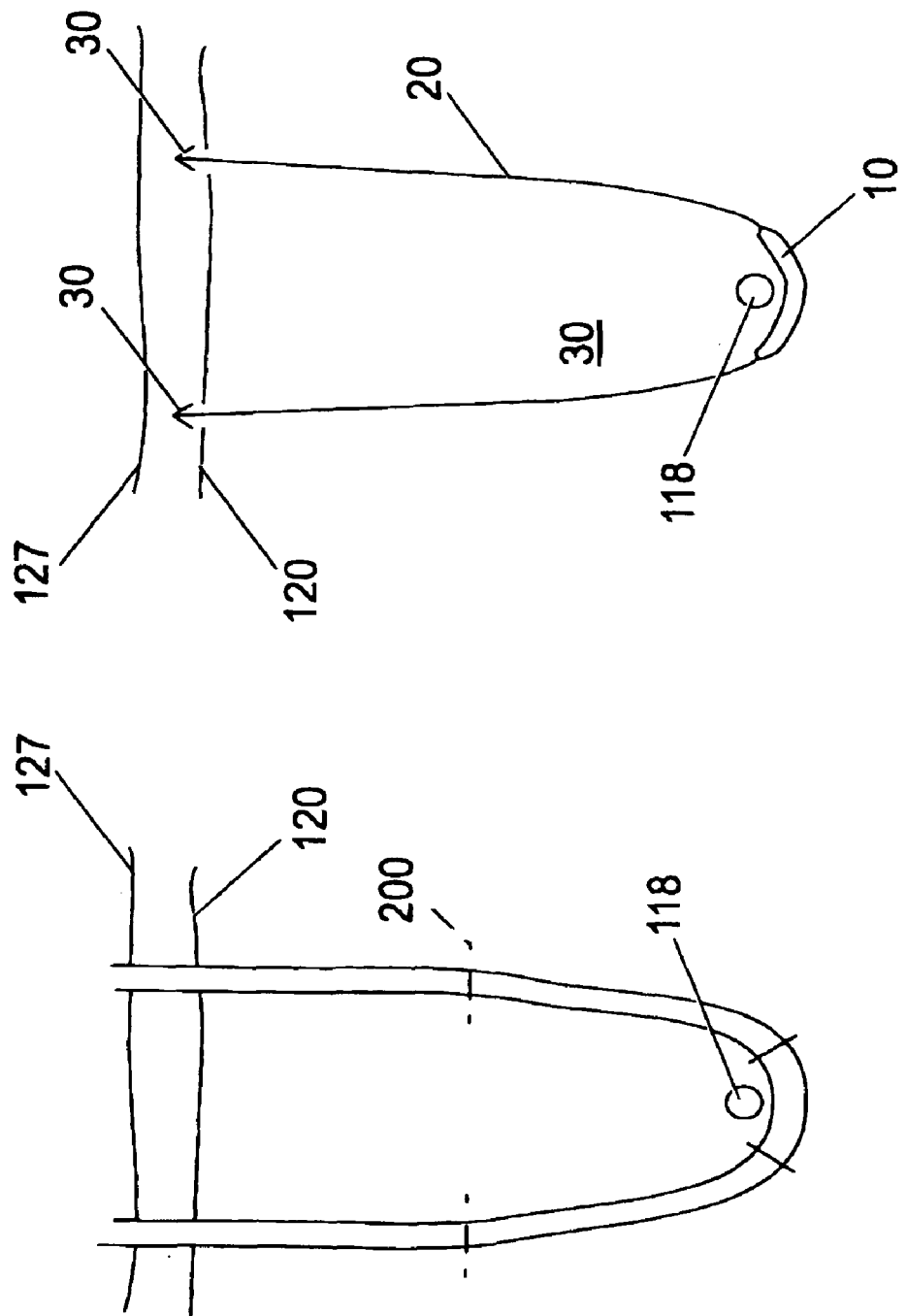
Figure 15:
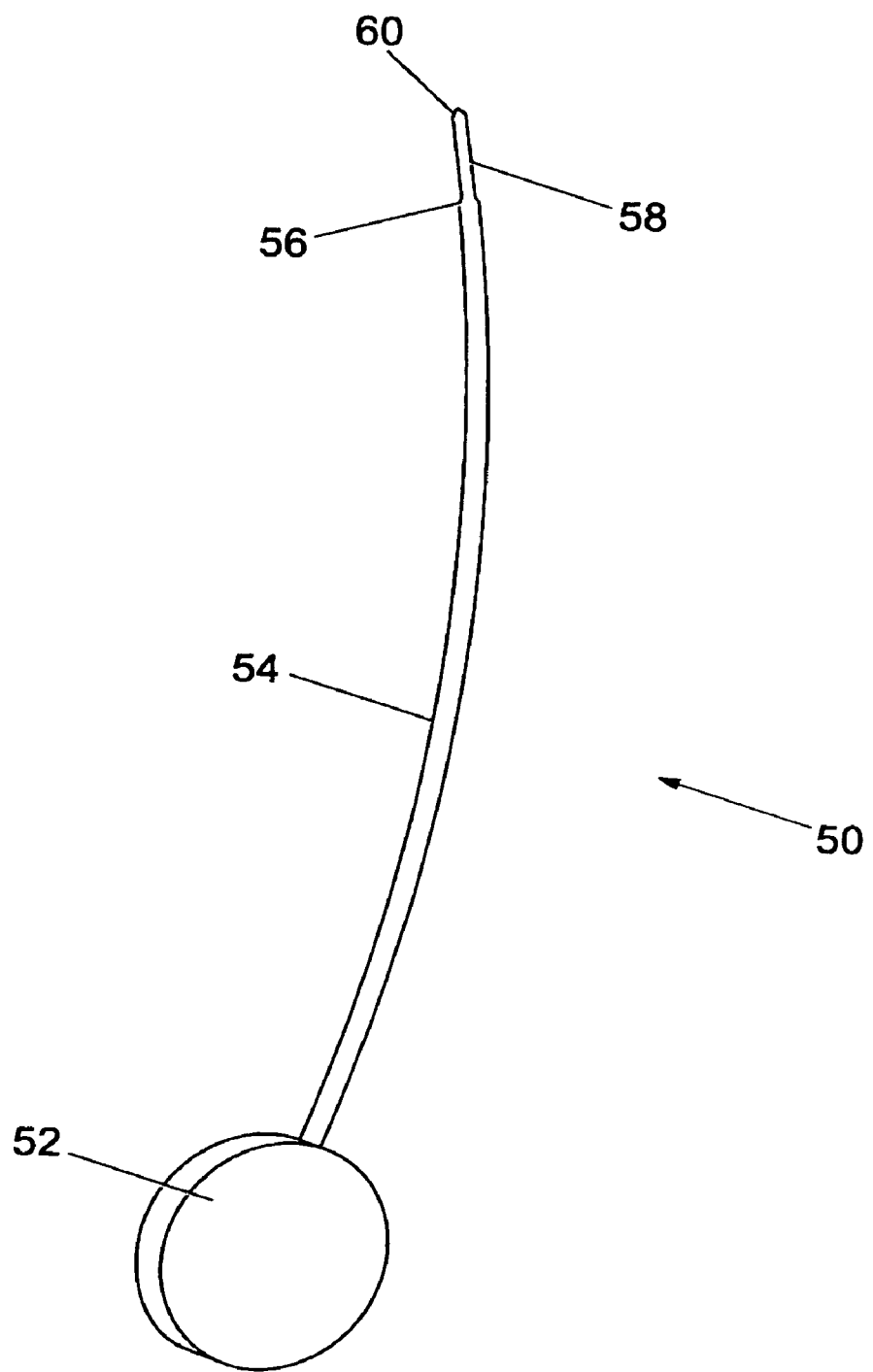
Figure 16:
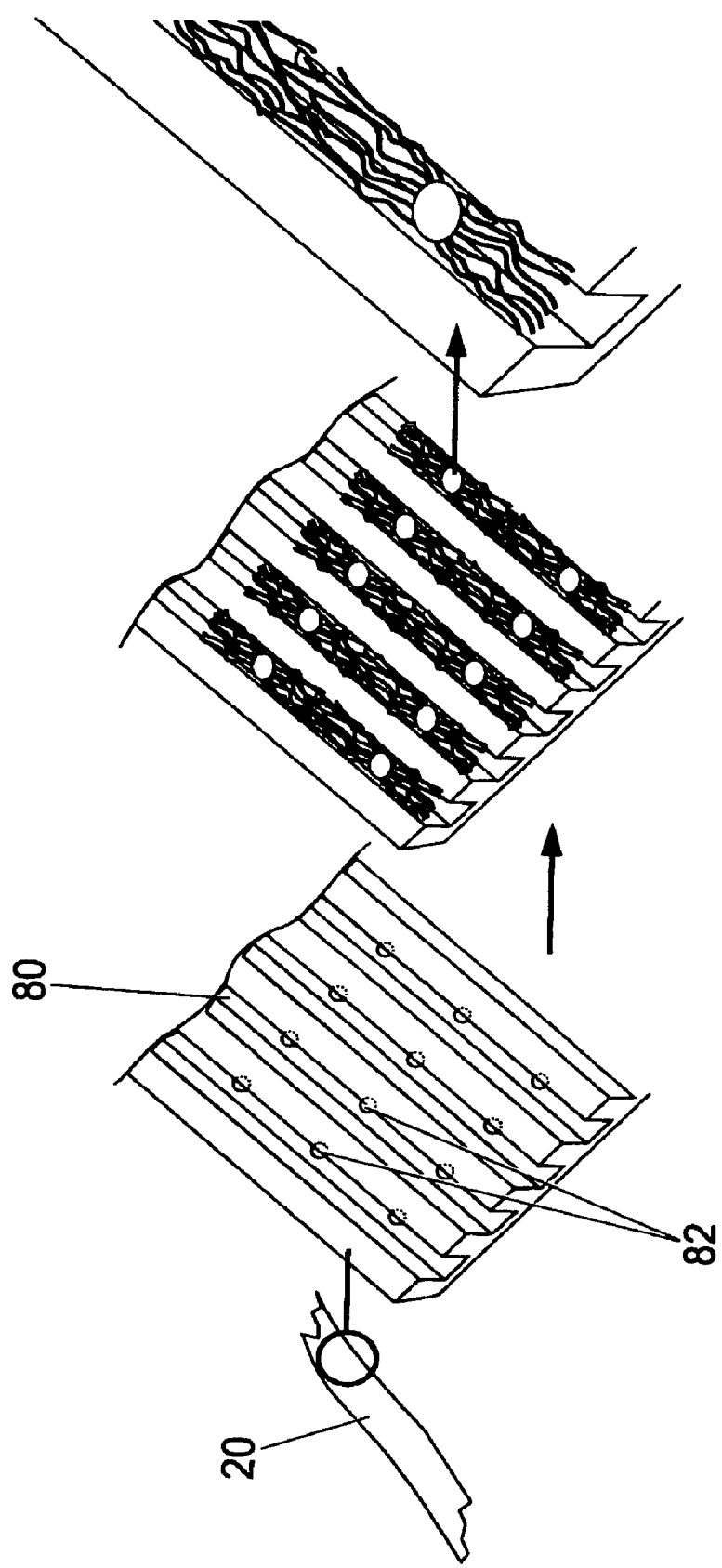

Preferred embodiments of the present invention will now be described, by way of example only, with reference to the accompanying drawings, in which:

FIG. 1 is an illustration of a surgical implant according to the invention,

FIG. 2 is a line drawing of the suspending means attached to the suburethral support, positioned underneath the urethra, FIG. 3 is an illustration of one embodiment of a suburethral support, FIG. 4 is an illustration of a second embodiment of a suburethral support, FIG. 5 shows suspending means being threaded through an attachment tab of a suburethral support, FIGS. 6A, B and C show alternative methods of attaching suspending means to a suburethral support, FIG. 7 is an illustration of a soft tissue anchor for insertion through the rectus sheath, FIGS. 8A-C are sequential illustrations of insertion of a soft tissue anchor of FIG. 7, FIG. 9 is an illustration of a soft tissue anchor mounted on an introducing tool, FIG. 10 is an illustration of a retropubic soft tissue anchor for use in the fibro-fatty tissues of the para-urethral tunnel, FIG. 11 is an illustration of the placement of a soft tissue anchor of FIG. 10, FIG. 12 is an illustration of an implanting tool and a soft tissue anchor inserted into the rectus sheath, FIG. 13 is an illustration of the surgical implant implanted into the rectus sheath, FIG. 14 is an illustration of the prior art contrasted with the technique of the present invention, FIG. 15 is an illustration of the tool used to insert the surgical implant, and FIG. 16 is an illustration of the surface architecture of the suspending means.

Referring to FIG. 1, a surgical implant for treating female urinary incontinence has a suburethral support 10, suspending means 20 and at least two soft tissue anchors 30, the suburethral support 10 being positioned in use, loosely under the urethra. The suburethral support has a length L of around 25 mm and a width W of around 10 mm such that it passes around the urethra with a minimum of excess material, although other similar dimensions would also be suitable. In this example, the suburethral support 10 is made from flat polymer tape. At each side 11,13 of the suburethral support 10 suspending means 20 are provided which attach to the suburethral support 10 at a first end 22,24.

The suspending means 20 are attached at a second end 26 to a respective soft tissue anchor 30.

As shown in FIG. 7 the soft tissue anchor 30 of the embodiment described comprises a central portion 32 and four winged sections 34 which are attached to the central portion at a first end 38 by resilient hinge means 36 and radially extend from the central portion 32 such that when viewed from the front the anchor device resembles a cross.

As shown in FIG. 8A the wing sections 34 of the soft tissue anchor 30 having a resting position in which they are inclined towards the rear 40 of the central portion 32 at an angle of around 45°. In FIG. 8B during penetration of the anchor through tissue (the point 60 of the introducing tool enabling the soft tissue anchor to be pushed through the tissue and rectus sheath 120) the wing sections 34 of the soft tissue element 30 may adopt a deflected position which means the penetration of the soft tissue anchor through the tissue and rectus sheath 120 is more effective.

As shown in FIG. 8C once the rectus sheath 120 has been pierced the resilient hinge means 36 cause the wing sections 34 to return to their resting position.

Movement of the soft tissue anchor in a direction opposite to which it was introduced into the soft tissue causes the wing section to be deflected until an endstop 46 is reached which prevents the wing sections 34 moving beyond a point substantially perpendicular to the central portion 32 and prevents retraction of the soft tissue anchor 30 from the soft tissue.

The soft tissue anchor 30 further comprises a hollow portion 48 which extends from the first end 38 to the second rear end 40 of the central portion 32 through which an introducing tool 50 may be placed.

The introducing tool 50 extends through the hollow portion 48 such that it extends as a sharp point 60 from the first end 38 of the soft tissue anchor 30 such that the sharp point 60 allows penetration of the tissue by the soft tissue anchor 30.

Stud like projections 42 which extend radially from the central portion 32 are angled such that they extend further radially from the central portion 32 as they extend towards the rear 40 of the central portion 32, this inclination allowing the soft tissue anchor 30 to pass more easily into the soft tissue.

A recessed portion 44 is positioned toward the rear end 40 of the central portion 32 to facilitate attachment of the suspending means 20 to the soft tissue anchor 30.

The suspending means 30 may be respectively attached to the soft tissue anchor 30 at this recessed point 44 by crimping a tube around the suspending means 20 to fix the suspending means 20 to the soft tissue anchor 30.

In the embodiment shown the soft tissue anchor may be suitably positioned in the rectus sheath 120 using an introducing tool 50. As shown in FIG. 15 the tool 50 comprises a handle 52 and elongate body 54. The elongate body 54 is curved through an angle of approximately 30° to facilitate positioning of the soft tissue anchor 30 in the rectus sheath or surrounding soft tissue of the human body from an incision in the upper wall of the vagina (as described below). The soft tissue anchor 30 is located on the elongate body at a narrowed portion 58 of the introducing tool such that the soft tissue anchor is held in place by an abutment 56 such that the narrowed portion 58 may extend through the hollow portion 48 of the soft tissue anchor 30 such that the point 60 of the insertion tool 50 protrudes from the first end 38 of the soft tissue anchor and allows the soft tissue anchor to be inserted into the human body through the soft tissues and more specifically through the rectus sheath 120 during the placement of the soft tissue anchor.

The placement of the soft tissue anchor 30 on the insertion tool 50 is shown in FIGS. 8B and 8C, which shows the soft tissue anchor 30 being pushed through soft tissue fascia, such as the rectus sheath 120. Once the soft tissue anchor has penetrated the rectus sheath fascia 120, as shown in FIG. 8B, the introducing tool 50 can be withdrawn, as shown in FIG. 8C, leaving the soft tissue anchor 30 in place.

As shown in FIG. 9 the soft tissue anchor may alternatively be comprised of a central portion 70 and a plurality of projections 72 the projections extending radially from the central portion 70 and arranged along a substantial portion of the length of the central portion 70. The projections 72 may be of any shape such that they provide resistance within the fibro-fatty soft tissue and blood tissues of the para-urethral tunnel in the direction opposite to that in which the soft tissue anchor is introduced.

This resistance is also provided by the multiple layers, typically between 5-10 layers of projections 72 which extend from the central portion 70.

Using these multiple layers of projections 72 it is not necessary to insert the soft tissue anchor through the rectus sheath 120. Instead the soft tissue anchor should be positioned as high in the retropubic space as possible in the fibro-fatty soft tissue.

In the embodiment of the soft tissue anchor comprising multiple layers of projections 72 which resembles a Christmas tree, as shown in FIG. 10, the introducing tool comprises a collar which releasably retains the projections during insertion into the retropubic space. The collar may comprise a semi-sharp bevelled needle. Following insertion of the Christmas tree like anchor into the fibro-fatty soft tissue of the retropubic space the introducing tool is withdrawn removing the collar from around the plurality of projections 72 of the soft tissue anchor, which due to their memory expand outwards from the central portion 70 and grip the fibro-fatty soft tissue of the retropubic space at multiple layers. The collar of the introducing tool which extends around the soft tissue may contain a cross-sectional opening such that once the tool is withdrawn the collar may be removed from the surgical implant by passing the implant through the cross-sectional opening.

Accordingly the invention also provides an introducing tool for use in inserting the soft tissue anchor.

Suspending means 20 attached to the soft tissue anchors are formed from a strip of plastics material such as polypropylene which is sufficiently soft to avoid damaging the urethra or surrounding body tissue and suitably inert such that it can be left in the human body for a long period of time without causing adverse reactions. Again, other suitable materials will be apparent to those skilled in the art.

The polypropylene mesh strip of 3-5 mm in width which forms the suspending means 20 has smooth edges to avoid adhesion of the soft tissue to the strip, reducing problems associated with leaving foreign material in the human body for long periods of time. As shown in FIG. 16 the polypropylene mesh strip further comprises pores or pits 80 ranging in width across the surface of the strip from 50 µm to 200 µm, which extend through the strip from a first surface of the strip 26 to a second opposite surface 28 of the strip the pores 80 allowing tissue in-growth to secure the suspending means 20 in the body.

The pores 80 are created by post synthesis treatment of the polypropylene mesh material by a laser.

The polypropylene mesh which forms the suspending means 20 also comprises microgrooves 82 of width 5 µm and of depth 5 µm on the surfaces of the polypropylene mesh.

The microgrooves 82 are aligned such that they are substantially parallel with each other and separated by ridges of around 5 µm in width.

The ridges are formed by square pillars the base of the microgroove being substantially perpendicular to the square pillars or bevelled in relation to the pillars. The microgrooving 82 being present on both surfaces of the suspending means to orientate and align the proliferating fibroblasts on the surface of the plastics material and cause axial alignment of collagen fibres and formation of at least one strong ordered neoligament.

This orientation and alignment of the proliferating cells adding mechanical strength to the tissue which forms around the plastics material such that it is more able to support the urethra.

The suburethral support is not provided with pores, pits or grooves to discourage the formation of peri-urethral adhesions.

Once the soft tissue anchors have been suitably positioned in either the soft tissue of the para-urethral tunnel or through the rectus sheath 120 the length of the suspending means 20 can be altered such that the suburethral support 10 hangs loosely under the urethra.

As shown in FIG. 2 the suspending means 20 are attached at a first end 22, 24 to the sides 12, 14 of the suburethral support 10, which extend on either side of the urethra.

Figure 6B:
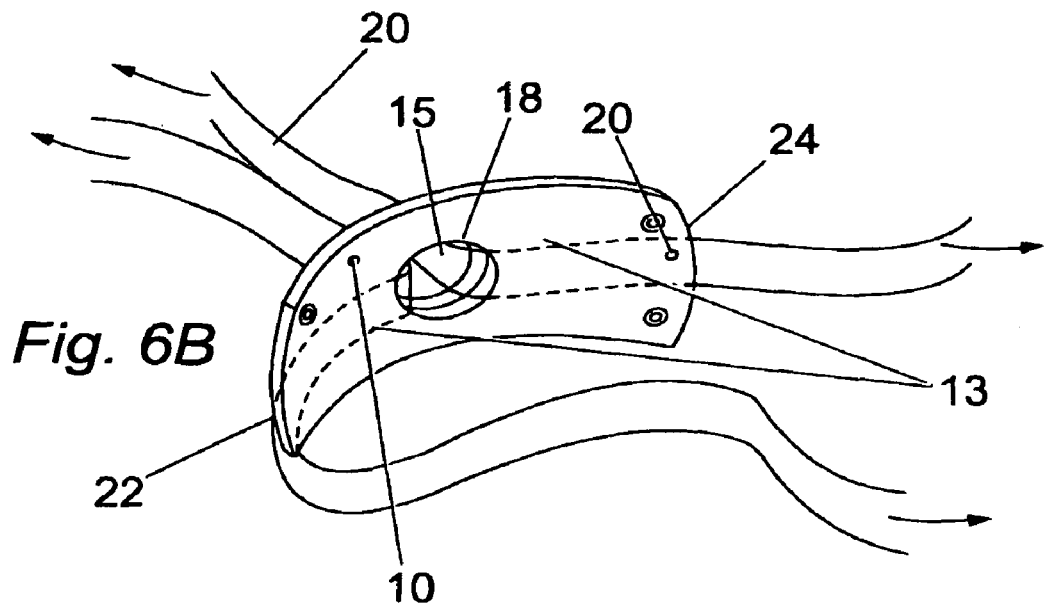
Figure 6C:
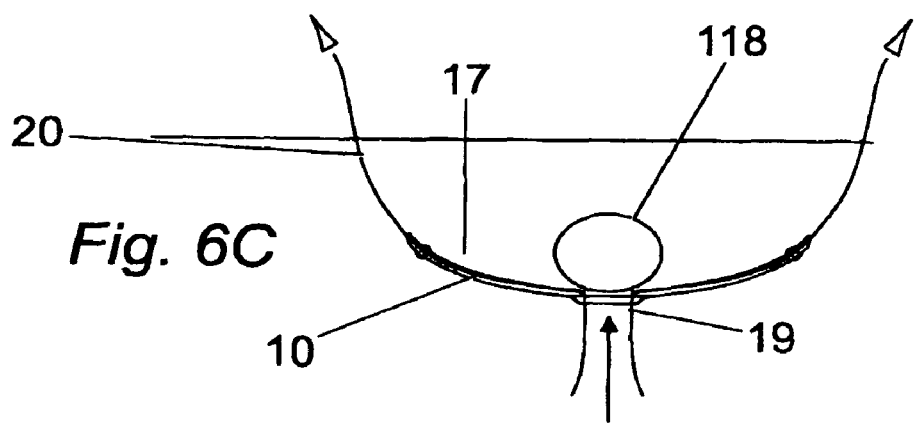

As shown in FIG. 6 a preferred method of altering the length of the suspending means 20 attached to the suburethral support 10 comprises a tunnelled element 13 at each of the free ends 22,24 of the suburethral support 10 on either side of the urethra. The tunnelled element 13 extends from the edges of the suburethral support 10 to an aperture 15, the aperture being present on the opposite surface 16 of the suburethral support 10 to the surface which contacts the urethra 17, the aperture 15 having an edge 18 able to co-operate with a ring element 19 such that the ring element which has memory can be pushed onto the edge 18 of the aperture 15 trapping the suspending means 20 between the edge of the aperture 18 and the ring element 19 thus securing the suburethral support 10 along a particular desired length of the suspending means 20 such that the suburethra support 10 hangs loosely under the urethra.

FIG. 5 shows an alternative method of attaching the suspending means 20 to the suburethral support 10, the suspending means 20 being threaded through jamming slots 12 such that the suspending means 20 are permanently attached to the jamming slots 12 by being pulled into the jamming slots 12 as shown in FIG. 5 such that the suspending means is held tightly in position.

Alternatively as shown in FIG. 6 the suspending means 20 may be passed through slots and the suspending means permanently attached to the slots by tying.

In use, as shown in FIG. 12 the soft tissue anchor 30 is placed on the introducing tool 50 as described above. An incision 117 is made in the upper wall 116 of the vagina, as shown in FIG. 11, and the introducing tool 112 is passed through the incision 117, past one side of the urethra 118, behind the pubic bone 119 and into the rectus sheath 120. It is apparent to the surgeon when the rectus sheath 120 has been penetrated as this stage of insertion presents significant resistance. Once the head 58 of the introducing tool 50 and the soft tissue anchor 30 have passed through the rectus sheath 120, the resistance diminishes and the surgeon ceases to insert the introducing tool 50.

The introducing tool 50 is retracted from the body releasing the soft tissue anchor 30. Due to the wing sections 34 on the central portion 32 of the soft tissue anchor 30, the soft tissue anchor 30 is retained by the rectus sheath 120 as the introducing tool 50 is retracted. Thus, the suspending means remains in the body, secured by the soft tissue anchor which is opposed by the rectus sheath 120.

This procedure is repeated, with a second soft tissue anchor 30 and suspending means 20, with the introducing tool 50 being passed through the incision 117 and past the other side of the urethra 118. Thus, two suspending means 20 are provided, attached to the rectus sheath 120, one passing either side of the urethra 118.

The suspending means 20 are passed through the tunnelled elements 13 of the suburethral support 10, and the suspending means 20 are pulled through the aperture 15 until the suburethral support 10 is positioned such that it passes under the urethra 118. The suspending means 20 are then fixed in place by placing a ring element 19 over the edge 18 of the aperture 15 such that the suspending means are trapped between the edge 18 and the ring element 19 securing them in place.

Alternatively as shown in FIG. 5 the suspending means may be fixed in the attachment tabs by threading them through jamming slots 12 or tying, as described above. The optimal lengths of the suspending means 20 are such that the suburethral support 10 passes under the urethra 118, but exerts no pressure on the urethra 118 unless the bladder 121 is displaced. The optimal positioning of the suburethral support 20 is roughly as illustrated in FIG. 14. When the bladder is displaced, the suburethral support 10 aids closure of the urethra 118, thus alleviating urinary incontinence.

In this example, a portion of the surgical implant is impregnated with methylene blue, which is a harmless water soluble dye. At the end of the procedure a small amount of fluid is expelled from the bladder 121. Should this fluid contain any dissolved methylene blue, it is very likely that the bladder has been perforated on placing the soft tissue anchor 30. In this case, cystoscopy should be carried out. If no methylene blue is present, the need for cystoscopy is advantageously obviated. Other suitable water-soluble dyes may, of course, be used.

Referring to FIG. 14, it can be appreciated that the surgical implant of the present invention, when inserted in the human body, may extend from the rectus sheath 120, through the paraurethral space 130 on one side of the urethra 118, around the urethra and back to the rectus sheath 120 on the other side. In contrast, the prior art device comprises a tape 200 that also extends through the abdominal wall 127 and represents a far greater implanted mass.

Referring to FIG. 11, in use, the further embodiment of soft tissue anchor illustrated in FIG. 9 for placement in fibro-fatty soft tissue of the retropubic space is placed on an introducing tool. An incision 117 is made in the upper wall 116 of the vagina, as shown in FIG. 11, and the introducing tool 112 is passed through the incision 117, past one side of the urethra 118, and located in the fibro-fatty soft tissue and blood vessels of the para-urethral tunnel. In this case the surgeon does not introduce the soft tissue anchor as far into the body as described previously and the rectus sheath 120 is not penetrated. Once the soft tissue anchor has been suitably positioned in the soft tissue the surgeon ceases to insert the introducing tool and retracts the introducing tool from the body releasing the projections of the soft tissue anchor 72. The release of the projections 72 of soft tissue anchor by the introducing tool allows the projections to grip the soft tissue surrounding the soft tissue anchor and provide resistance to movement of the soft tissue anchor in a direction opposite to that which it was inserted.

This procedure is repeated, with a second soft tissue anchor such that the projections 72 of the soft tissue anchor also provide resistance to movement of the soft tissue anchor in a direction opposite to that which it was inserted the introducing tool being passed through the incision 117 and past the other side of the urethra 118.

Thus, two suspending means 20 are provided, which are held in the soft tissue comprising fibro-fatty tissue and blood vessels.

As described above the suspending means 20 are passed through the attachment tabs of the suburethral support 10, and the suburethral support 10 positioned such that it passes under the urethra 118.

Again this device contrasts that described by the prior art device in that it does not extend through the abdominal wall 127 and does not represent as much implanted mass.

Various embodiments of the present invention can be envisaged within the scope of the invention, for example the soft tissue anchor may comprise a cone or a half cone such that a circular or semi-circular base is provided as a retaining means to prevent retraction of the soft tissue anchor in a direction opposite to that in which it is inserted into the tissue.

Alternatively the soft tissue anchor may comprises a substantially flat or disc shaped head. In this case the introducing tool may have a conical head with a sharp point at its apex and a slot for receiving the flat or disc shaped head.

In yet another example, the soft tissue anchor may be formed of two sections. The upper section, i.e. the portion of the anchor that forms the sharp point 10, may be made from an absorbable material, such as polyglactin such that a sharp point is provided for insertion of the anchor into the body, but this sharp point is later absorbed by the body so as to eliminate any discomfort or disadvantage caused by a sharp pointed object being retained inside the body.

The soft tissue anchor may be made from metal, such as titanium, as this is a hard material that can easily be formed into the head having the sharp point at its apex, and is sufficiently malleable to provide a tube that may be crimped to the suspending means.

The invention claimed is:

1. A method for providing support to a urethra in a patient comprising the steps of:
   (a) introducing through an incision in the vaginal wall, a surgical implant comprising, a suburethral support, at least two soft tissue anchors, and at least two suspending strips, each suspending strip extending between the suburethral support and one of the at least two soft tissue anchors;
   (b) positioning the suburethral support under the urethra;
   (c) introducing one of said at least two soft tissue anchors through a para-urethral tunnel on one side of the urethra;
   (d) introducing the other of said at least two soft tissue anchors through a para-urethral tunnel on the other side of the urethra; and
   (e) positioning each of said soft tissue anchors in tissue comprising soft tissue without penetrating the rectus sheath.

2. The method according to claim 1 wherein said suburethral support is joined to said suspending strip by an attachment tab.

3. The method according to claim 2 wherein said joining of said attachment tab is releasable.

4. The method according to claim 1 wherein the soft tissue anchors may be repositioned within the soft tissue to adjust the position of the suburethral support.

5. The method according to claim 1 further comprising introducing a tool into the soft tissue for accessing and placing one or more of the soft tissue anchors in said soft tissues, wherein the tool comprises a housing for receiving the one or more soft tissue anchors.

6. The method according to claim 1 wherein the method provides support to the urethra for treating incontinence.

7. The method according to claim 1 wherein the method provides support to the urethra for treating a uterovaginal prolapse.

8. The method according to claim 1 wherein the soft tissue comprises fibro-fatty tissue.

9. The method according to claim 1 wherein positioning said soft tissue anchors comprises positioning a plurality of projections extending from said soft tissue anchors into said soft tissue.

10. The method according to claim 1 wherein positioning said suburethral support comprises positioning a suburethral support having a length in the range of about 15-35 mm and a width in the range of about 5-15 mm under the urethra.

11. The method according to claim 1 wherein the position of the suburethral support is adjustable by adjusting the length of the suspending strip.

\* \* \* \* \*